United States Patent [19]
Marras et al.

[11] Patent Number: 5,094,249
[45] Date of Patent: Mar. 10, 1992

[54] APPARATUS FOR MONITORING THE MOTION OF THE LUMBAR SPINE

[75] Inventors: William S. Marras, 225 Beach Trail Ct., Powell, Ohio 43065; Robert J. Miller, Westerville, Ohio; Shelby W. Davis, Amlin, Ohio; Gary A. Mirka, Brecksville, Ohio

[73] Assignee: William S. Marras, Powell, Ohio

[21] Appl. No.: 719,650

[22] Filed: Jun. 21, 1991

Related U.S. Application Data

[63] Continuation of Ser. No. 509,679, Apr. 16, 1990, abandoned.

[51] Int. Cl.⁵ .............................................. A61B 5/11
[52] U.S. Cl. ................................. 128/781; 73/379; 272/134
[58] Field of Search ......................... 128/774, 781, 782; 272/129, 130, 131, 132, 134, 137–139, 140, 146; 73/379, 380, 381

[56] References Cited

U.S. PATENT DOCUMENTS

| | | | |
|---|---|---|---|
| 4,113,250 | 9/1978 | Davis | 272/146 |
| 4,462,252 | 7/1984 | Smidt et al. | |
| 4,492,236 | 1/1985 | Pile | 128/781 |
| 4,565,368 | 1/1986 | Boettcher | |
| 4,702,108 | 10/1987 | Amundsen et al. | |
| 4,732,381 | 3/1988 | Skowronski | |
| 4,805,455 | 2/1989 | DelGiorno et al. | |
| 4,824,103 | 4/1989 | Smidth | |
| 4,893,808 | 1/1990 | McIntyre et al. | 272/134 |

OTHER PUBLICATIONS

The Low Back Machine that Moves Like the Low Back; Isotechnologies, Inc.; 1 page brochure.
The Isostation B-200; 1 page brochure.
Cybex Back Systems-Trunk Extension/Flexion Unit; 1 page brochure.
Cybex Back Systems—Torso Rotation Unit; 1 page brochure.

*Primary Examiner*—William E. Kamm
*Assistant Examiner*—Scott R. Akers
*Attorney, Agent, or Firm*—Bell, Seltzer, Park & Gibson

[57] ABSTRACT

An apparatus is disclosed for monitoring the movement and force production of the lumbar spine during flexion and extension in each of several sagittal-frontal planes of the body, as well as during movement into he transverse (twisting) plane. The apparatus includes a rotatable platform upon which the patient is adapted to stand, and the platform is pivotable about a vertical axis, so that the platform may be pivoted to a selected angle and locked in position. A pelvic stabilization belt is mounted to the platform, and an overhead frame member is provided for rotation about a horizontal axis which is adapted to pass through the lumbro-sacral junction of the patient. An upper body yoke is mounted to the overhead frame member for rotation about a generally vertical axis which is perpendicular to the horizontal axis. An upper body engaging member is mounted to the yoke, and a control system is provided whereby the apparatus may be operated in a flexion/extension mode, or in a twisting mode, and with the foot platform in a selected angular position.

22 Claims, 4 Drawing Sheets

APPARATUS FOR MONITORING THE MOTION OF THE LUMBAR SPINE

This application is a continuation of application Ser. No. 509,679, now abandoned, filed Apr. 16, 1990.

BACKGROUND OF THE INVENTION

The present invention relates to an apparatus for monitoring the movement and force production of the lumbar spine during flexion and extension of the trunk of a patient in each of several sagittal-frontal planes of the body, and during trunk twisting. The apparatus is useful in the design of ergonomically suitable workplaces, and in the analysis and rehabilitation of low back disorders.

Occupationally related low back disorders have become a problem of epidemic proportion in the industrialized world in recent years, and has been recognized as a major problem in the industrial environment. It is widely known that the majority of low back disorders associated with the workplace involve muscular overexertion injuries. These injuries occur frequently and are quite acute initially but may progress to a more chronic state with repetitive strains. One of the basic concepts in the ergonomic control of the workplace is to design manual materials handling tasks so that the strength required by the task does not exceed most workers capabilities.

Worker strength has traditionally been evaluated using isometric strength tests of workers in the sagittal plane, i.e. the extension/flexion plane. The machines which are currently marketed for measuring movement in the sagittal plane are of limited utility, however, since they can not assess motion components that are commonly found in the workplace or everyday life, and which are asymmetric. Machines of this general type are illustrated, for example, in U.S. Pats. to Smidt et al, No. 4,462,252 and Boethcher, No. 4,565,368. Also, a similar machine is sold by Cybex, a division of Lumex, Inc. of Bay Shore, NY, as the Cybex TR unit.

Machines are also available for assessing movement in the transverse (i.e. twisting) plane, and a machine of this general type is manufactured by Cybex, as the Cybex TEF unit. Note also the U.S. Pat. to Skowronski, No. 4,732,381. Here again, however, these machines are of limited utility in that they are unable to assess commonly encountered motions which include components in addition to twisting.

Isotechnologies Inc., of Hillsboro, NC, currently markets a low back testing and rehabilitation machine under the designation Iso Station ® B-200, which includes a fixed platform upon which the patient stands, and a stabilizing belt system for locking the legs in a fixed upright position while the patient stands on the platform. The upper body is attached to a harness arrangement, which permits the upper body to move in three planes while the legs are fixed, namely the flexion/extension plane, the transverse (twisting) plane, and the lateral flexion plane. The apparatus also permits bending outside of the sagittal plane during flexion/extension movement. The movements in each of these planes are monitored, with the apparatus operated either dynamically or isometrically.

While the above described Iso Station ® machine is better able to assess complex motion as compared to the above described single function machines, it does not permit the assessment of the lumbar movement of the spine in any specifically selected plane or combination of planes, since there is no control of the path of movement of the upper trunk. Thus there is an inherent inability to interpret the results accurately with respect to workplace determined demands, since patients produce different motions.

It is accordingly an object of the present invention to provide an apparatus for monitoring the movement of the lumbar spine which permits movement in a number of motion planes, and with the path of movement of the patient in each selected plane, or combination of planes, being controlled by the machine.

It is a more particular object of the present invention to provide an apparatus which is able to monitor the movement of the lumbar spine during trunk bending in the flexion/extension plane, both symmetrically, i.e. within the sagittal plane, and asymmetrically, i.e. outside of the sagittal plane.

It is a further object of the present invention to provide an apparatus for monitoring the movement of the lumbar spine and which may be selectively configured to monitor the motion components during bending in the flexion/extension plane, or during movement in the transverse plane, and while assuming a symmetric or asymmetric trunk position.

SUMMARY OF THE INVENTION

The above and other objects and advantages of the present invention are achieved in the embodiment illustrated herein by the provision of an apparatus which comprises a main frame, and a horizontal platform which is rotatably mounted to the main frame for rotation about a vertical axis and which is adapted to support a patient in a standing position thereupon. The platform may be locked to the main frame in each of several predetermined rotational positions with respect to the main frame, and pelvic stabilization means is mounted to the platform for releasable connection to the pelvic region of the trunk of a patient standing upon the platform so as to support the pelvic region of the trunk in a fixed position with respect to the platform.

A frame member is mounted to the main frame for rotation about a horizontal axis which is positioned to pass approximately through the lumbro-sacral junction of a patient while the patient is standing upon the platform and supported by the pelvic stabilization means, and upper body engaging means is mounted to the frame member for engaging the upper body portion of a patient standing upon the platform and so that flexion and extension of the trunk of the patient causes the frame member to pivot about the horizontal axis in at least one direction. Dynamometer means is operatively connected to the frame member for controlling the pivotal movement thereof in each pivotal direction. In use, the platform may be selectively moved to each of the predetermined rotational positions and the patient permitted to perform flexion and extension of the trunk about the horizontal axis while the platform is in each of the positions, and while the dynamometer means controls the pivotal movement of the frame member.

In the illustrated and preferred embodiment, the apparatus is further capable of monitoring the movement of the lumbar spine during movement about the transverse, or twisting plane. For this purpose, the above described frame member comprises an overhead member of generally U-shaped outline which comprises a horizontal beam and two depending legs. Also, an upper body yoke is provided which is mounted to the horizontal beam of the overhead frame member for rotation about a twisting axis which is generally vertical and perpendicular to the horizontal axis. In addition, means is provided for selectively converting the apparatus to a first configuration wherein the upper body yoke is locked against rotation about the twisting axis, while the overhead frame member is free to rotate about the horizontal axis. In a second configuration, the overhead frame member is locked against rotation about the horizontal axis, while the yoke is free to rotate about the twisting axis. The dynamometer means controls pivotal movement of the overhead frame member when in the first configuration, and controls twisting movement of the upper body yoke when in the second configuration. Thus when in the first configuration, the patient is permitted to perform flexion and extension of the trunk about the horizontal axis, while the dynamometer means controls the pivotal movement of the overhead frame member, and in the second configuration, the patient is permitted to perform twisting of the trunk, while the dynamometer means controls the twisting movement of the upper body yoke. In either mode, the trunk may be positioned in a symmetric or asymmetric position, by rotation of the platform to a selected rotational position.

The dynamometer means of the apparatus preferably also comprises a first force transducer for measuring the force applied between the overhead frame member and the patient when the apparatus is in the first configuration, and a second force transducer for measuring the twisting force applied between the upper body yoke and the patient when the apparatus is in the second configuration. Further, a first potentiometer is provided for monitoring the angular position of the overhead frame member when the apparatus is in the first configuration, and a second potentiometer is provided for monitoring the angular position of the yoke when the apparatus is in the second configuration. The dynamometer means further comprises a reversible drive motor, and a computer control system which includes a predetermined program for monitoring the output signals from the two transducers and the two potentiometers, and for controlling the operation of the drive motor in accordance with the program when the apparatus is in each of the first and second configurations.

BRIEF DESCRIPTION OF THE DRAWINGS

Some of the objects and advantages of the present invention having been stated, others will appear as the description proceeds, when taken in conjunction with the accompanying drawings, in which.

DETAILED DESCRIPTION OF THE PREFERRED EMBODIMENTS

Figure 1:
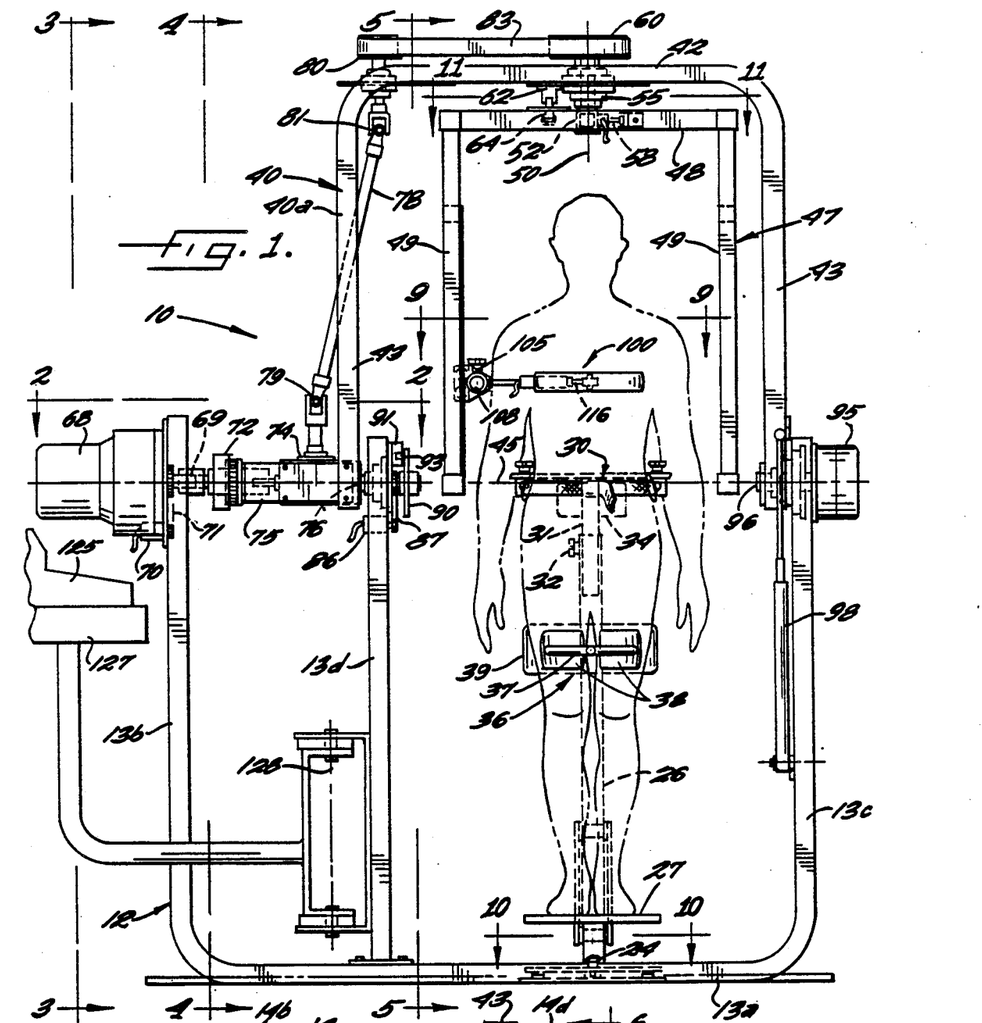
FIG. 1 is a front elevation view of an apparatus for monitoring the motion of the lumbar spine which embodies the present invention, and with the apparatus configured for fexion and extension movement of the patient in the sagittal plane.

Referring more particularly to the drawings, an apparatus which embodies the features of the present invention is indicated generally at 10. The overall apparatus 10 is best seen in FIG. 1, and it comprises a main frame 12, which is composed of a pair of generally U-shaped base members 13, 14, and with each base member comprising a horizontal ground engaging leg 13a, 14a and a pair of laterally spaced apart upright legs 13b, 13c, 14b, 14c. Also, a pair of intermediate upright legs 13d, 14d extends upwardly from the two ground engaging legs.

Figures 5, 9, 10, 11:
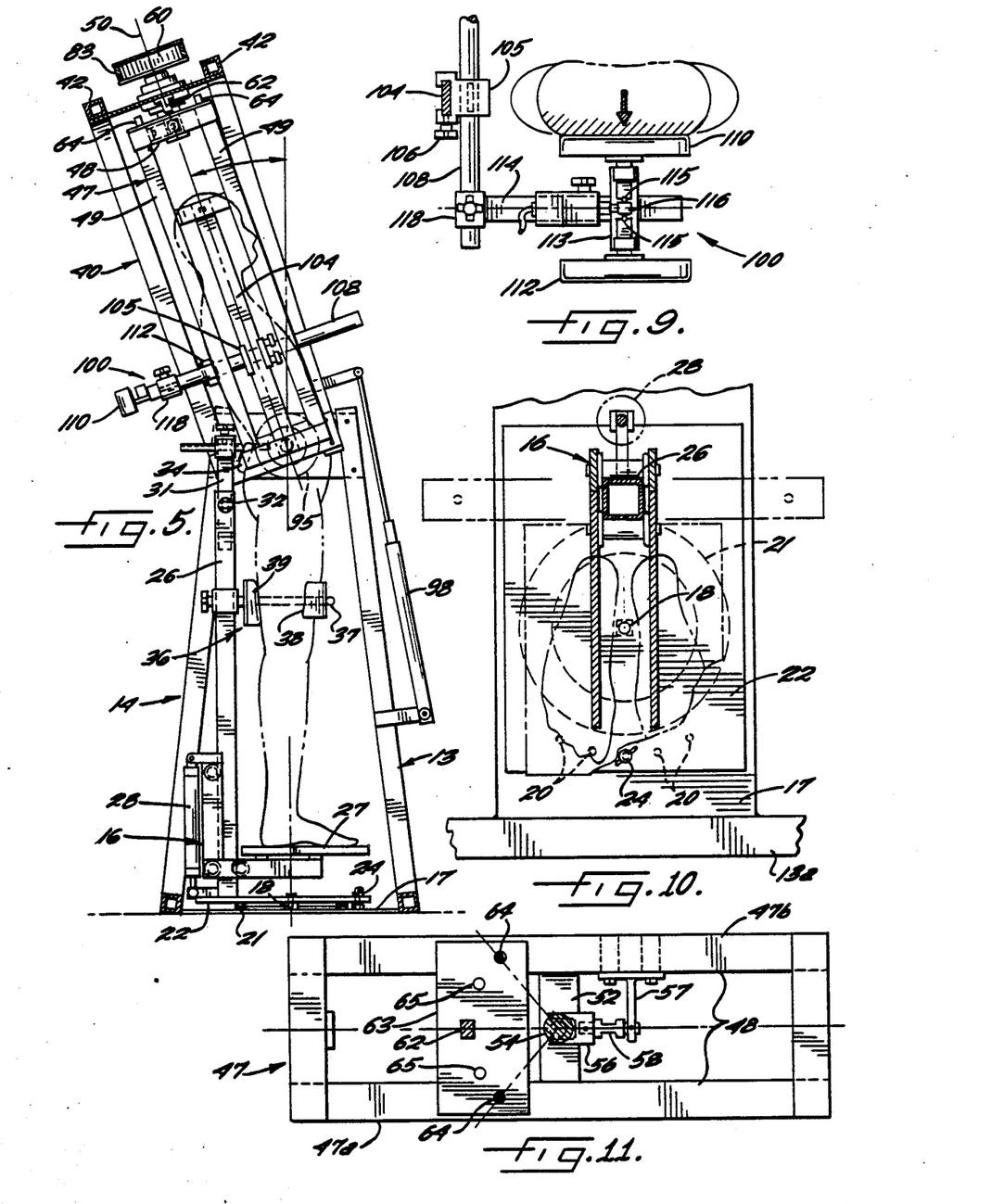
FIG. 9 is a fragmentary plan view illustrating the upper body engaging member used in the flexion/extension mode; and taken substantially along the line 9—9 of FIG. 1.
FIG. 10 is a fragmentary plan view of the base for the foot engaging platform if the apparatus, and taken substantially along the line 10—10 of FIG. 1.
FIG. 11 is a fragmentary plan view of the means for mounting the upper body yoke for rotation about the twisting axis, and taken substantially along the line 11—11 of FIG. 1.

A platform assembly 16 is mounted to the lower portion of the main frame and generally between the two ground engaging legs 13a, 14a of the two U-shaped base members 13, 14. The platform assembly 16 includes a base plate 17 which is fixed between the two ground engaging legs 13a, 14a, and as best seen in FIG. 10, the base plate 17 mounts a vertical pivot pin 18, and it includes a number of openings 20 positioned on an arc centered at the pivot pin, for the purpose described below.

A bearing plate 21 is mounted immediately above the base plate 17, and a pivot plate 22 is positioned to rest upon the bearing plate 21 so as to permit rotation about the axis of the pivot pin 18. The pivot plate 22 includes an opening which mounts a removable detent 24, which is designed to be received in a selected one of the openings 20 of the base plate, to rotatably lock the pivot plate in a selected rotational position.

The platform assembly 16 further includes a vertical post 26 which extends upwardly from the pivot plate 22. A horizontal platform 27, which is adapted to support a patient in a standing position thereupon, is mounted for sliding movement along the vertical post 26, and the elevation of the platform on the post is controlled by an electric linear actuator 28 so as to permit the apparatus to accommodate patients of varying height.

In the illustrated embodiment, the base plate 17 includes a total of five spaced-apart openings 20 which are adapted to be selectively aligned with the opening in the pivot plate 22 when the pivot plate and platform are pivoted about the axis of the pin 18. Typically, the openings 20 are positioned so that the central opening defines symmetric movement along the sagittal plane in the manner further described below, whereas the outside openings permit asymmetric movement at either 15° or 30° on each side of the central opening, note FIGS. 12 and 13.

Figures 3, 4, 6, 7, 8:
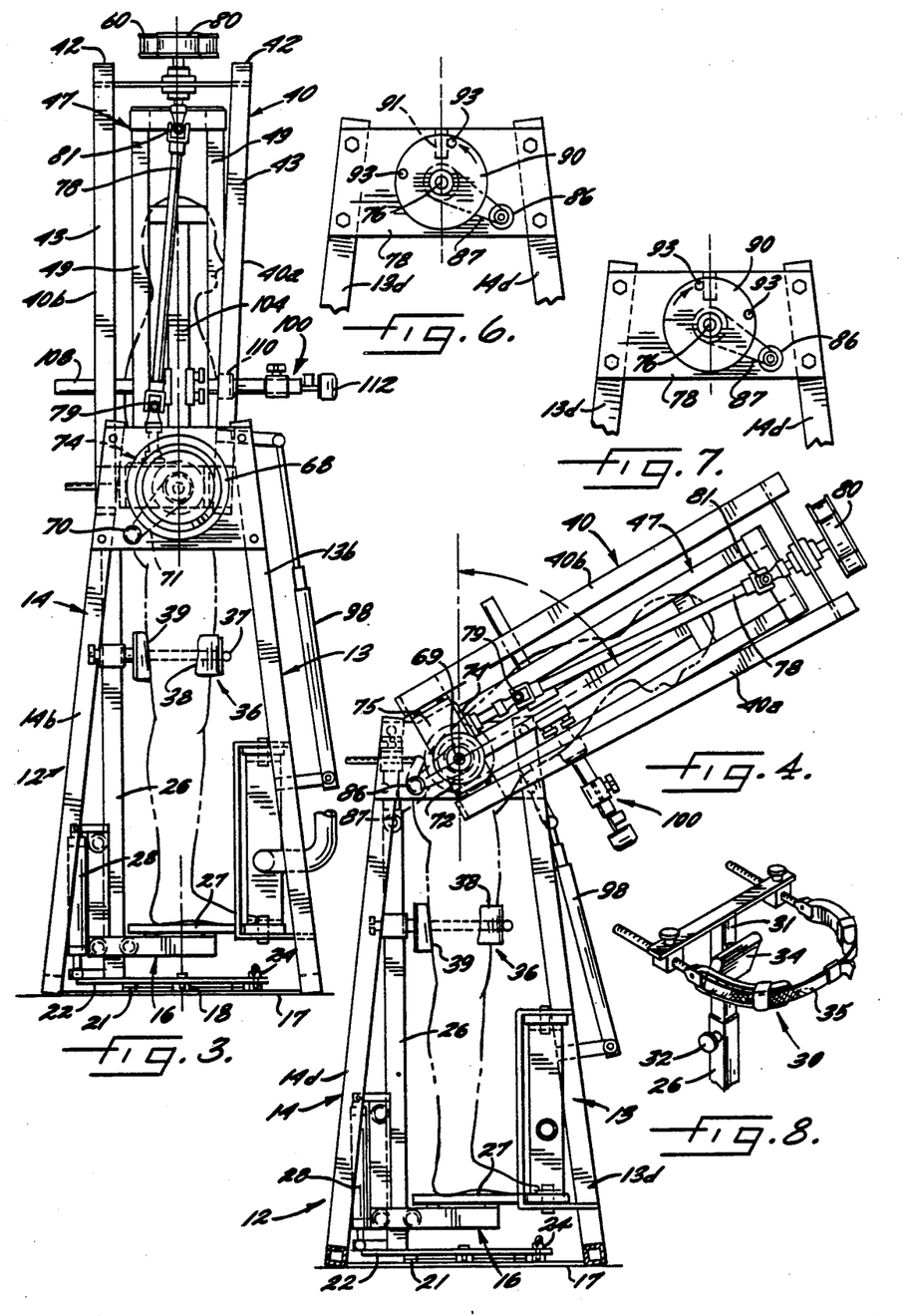
FIGS. 3-5 are side elevation views of the apparatus, shown in the fully upright, forwardly inclined, and rearwardly inclined positions respectively.
FIGS. 6 and 7 are fragmentary sectional views taken along the line 6—6 of FIG. 2, and illustrating the maximum forward position and maximum rearward position, respectively.
FIG. 8 is a perspective view of the pelvic stabilization assembly of the apparatus.

The upper end of the post 26 mounts a pelvic stabilizing assembly 30 as best seen in FIG. 8, which comprises a slide rod 31 positioned within the post 26, and a threaded pin 32 for locking the slide rod at a selected elevation with respect to the platform. The pelvic stabilization assembly 30 also includes a lower back pad 34 which is mounted to the slide rod 31, and a releasable waist band 35 which is adapted to firmly surround and support the pelvic region of the patient. Also, there is provided a leg engaging assembly 36 which includes a rod 37 which is slidably mounted on the post 26 and which is adapted to extend between the legs of the patient. A pair of padded front thigh pads 38 are mounted to the rod 37 for engaging each leg immediately above the knee and so as to press the same rearwardly against a pair of rear thigh pads 39. The legs are thereby firmly locked in the extended position in the illustrated embodiment of the apparatus. As opposed to the illustrated locked fully extended position of the legs, it will be understood that the apparatus may be designed to permit monitoring with the legs in a locked fully flexed position.

The apparatus of the present invention also includes an overhead frame member 40 having a generally inverted U-shaped outline, which is composed of a pair of forward and rear frame members 40a, 40b of corresponding outline. The two frame members 40a, 40b collectively define a horizontal beam 42 and two depending legs 43. Means are provide for mounting the overhead frame member to the main frame for movement about a horizontal axis 45 which is positioned to extend through both of the depending legs 43, and with the horizontal beam 42 being parallel to and above the horizontal axis 45.

An upper body yoke 47 is also provided, and which has a U-shaped outline and which is also composed of a pair of forward and rear frame members 47a, 47b of corresponding outline. The two frame members 47a, 47b collectively define a horizontal arm 48 and two depending arms 49, and the yoke is sized so as to permit the yoke to fit within the outline of the overhead frame member 40. The upper body yoke 47 is mounted to the horizontal beam 42 of the overhead frame member for rotation about a twisting axis 50 which is generally vertical and perpendicular to the horizontal axis.

As best seen in FIG. 11, the mounting structure for the yoke 47 comprises a plate 52 which is fixed to the horizontal arm 48 of the yoke 47, and a shaft 54 which extends perpendicularly through the horizontal arm and the plate 52, and which defines the twisting axis 50. The shaft 54 is rotatably mounted to the overhead frame member 40 and to the plate 52 by means of bearings 55, and the torque is transmitted from the shaft 54 to the yoke 47 via a transmission assembly which includes a bracket 56 which is keyed to the shaft so as to be locked against rotation with respect to the shaft. A second bracket 57 is fixed to the arm 48 of the yoke, and a load cell 58 is mounted between the two brackets 56, 57 so as to measure the torque imparted between the overhead frame member and the yoke. Also, the upper end of the shaft 54 mounts a drive pulley 60, such that rotation of the pulley 60 causes a corresponding rotation of the yoke about the twisting axis 50.

Referring again to FIG. 11, a yoke stop 62 is fixed to the overhead frame member 40, and a second plate 63 is fixed to the yoke below the stop. Also, the plate 63 includes a pair of pins 64 which are mounted along an arc centered at the shaft 54, and the pins 64 are each adapted to engage the stop 62 and thereby physically limit the twisting rotation of the yoke with respect to the overhead frame member to about 45° in each direction. The plate 63 also includes a pair of openings 65 which are aligned on the same rotational arc, and which are adapted to selectively receive a removable detent (not shown) so as to physically engage the stop and limit rotation to about 20° in one or both directions.

The apparatus 10 further includes dynamometer means which is mounted to the frame 12 for controlling pivotal movement of the overhead frame member 40 and twisting movement of the upper body yoke 47, in the manner described in more detail below. The dynamometer means includes a conventional permanent magnet reversible DC servo motor 68, which is operable at a variable speed, and which includes a built-in reduction gear box. A motor of this type is manufactured by PMI Motion Technologies of Commack, NY, as Model No. JR16M4CH.

Figure 2:
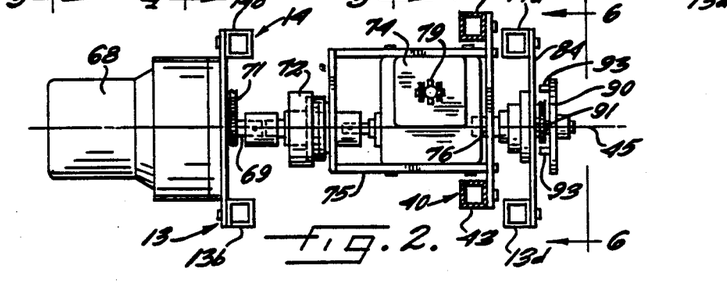
FIG. 2 is a fragmentary plan view of a portion of the drive system of the apparatus, and taken substantially along the line 2—2 of FIG. 1.

As best seen in FIG. 2, the output shaft 69 of the motor is coaxial to the horizontal axis 45, and it is connected to a potentiometer 70 via a belt drive 71, which registers the rotational position of the motor. The output shaft 69 is also connected to a clutch 72, and to a 90° gear box 74. The output of the clutch is fixed to a boxlike frame member 75 which is connected to the housing of the 90° gear box 74 and to a second output shaft 76, which is coaxial with the horizontal axis 45, and which in turn is fixedly connected to one of the legs 43 of the overhead frame member 40 The output of the 90° gear box 74 is connected to an upwardly directed drive shaft 78 through a universal joint 79, and the opposite end of the drive shaft 78 is connected to a pulley 80 through a second universal joint 81. The pulley 80 is rotatably mounted to the overhead frame member 40, and a drive belt 83 is entrained about the pulley 80 and the pulley 60 which is connected to the twisting shaft 54.

The second output shaft 76 is rotatably mounted to a plate 84 which is fixed to the upper ends of the intermediate legs 13d, 14d of the frame, and a potentiometer 86 is operatively connected to the shaft 76 via a belt drive 87 to register the rotational position of the shaft 76 and thus the overhead frame member 40.

To physically limit the angular movement of the overhead frame member 40, a disc 90 is fixedly mounted to the shaft 76, so as to overlie the plate 84. The plate 84 mounts a stop 91, and the disc 90 mounts a pair of pins 93 which contact the stop 91 to physically limit the rotation of the overhead frame member 40 in each rotational direction from its upright or overhead position. As best seen in FIGS. 6 and 7, the pins 93 typically are positioned so that the overhead frame member 40 is able to rotate about 60° in the forward (flexion) direction from the upright position, and about 20° in the rearward (extension) direction. The disc 90 may, if desired, also include openings for receiving a removable pin, which can shorten the rotational limits in each direction.

An electric brake 95 is also mounted to the main frame 12 along the horizontal axis, and on the opposite side of the overhead frame member 40. The brake is fixedly connected to the member 40 via a shaft 96 so as to be adapted to hold the frame member rigid in a vertical position, or at any other selected rotational position.

Also, a gas spring 98 is mounted between the main frame 12 and the overhead frame member 40, which serves to counterbalance and dampen the movement of the overhead frame member in each direction.

In operation, when the clutch 72 is open, the output shaft 69 operates through the 90° gear box 74 to rotate the drive shaft 78 and pulleys 80, 60, and thus pivot the yoke 47 about the twisting axis 50. The brake 95 may be actuated in this mode to hold the overhead frame member against rotation about the horizontal axis 45. When the clutch is closed and the brake is released, the frame member 75, the 90° gear box 74, and the output shaft 76 all rotate about the horizontal axis 45 to pivot the overhead frame member 40 and the yoke about the axis 45.

The apparatus 10 also includes two separately usable upper body engaging members 100 and 102 for engaging the upper body portion of the patient standing upon the platform, with each body engaging member being usable in one of the two primary modes of operation. Each of the two body engaging members 100, 102 is mounted to one of the depending arms 49 of the yoke. In this regard, the selected depending arm 49 includes a vertical mounting plate 104, and a slide 105 which is mounted to the plate 104 for slidable movement along the direction of the arm. Also, a threaded pin 106 (FIG. 9) is provided for locking the slide at a selected elevation. The slide 105 in turn mounts a generally horizontal utility rod 108, which extends along a direction extending perpendicularly to the horizontal axis 45 and generally between the back and front of the patient standing upon the platform 27.

The first body engaging member 100 is best seen in FIG. 9, and is used when the apparatus is configured for operation in the flexion/extension mode. The first member 100 comprises a pair of elongate pads 110, 112 which are mounted together for limited sliding movement on a cross arm 113. The cross arm 113 is fixed to a support arm 114, and each pad 110, 112 mounts a pin 115 which are positioned to engage a load cell 116 which indicates the force applied laterally between either one of the pads 110, 112 and the support arm 114. The support arm 114 includes a sleeve 118 at the remote end thereof for slidably mounting to the utility rod 108. Thus when the patient is to undergo flexion (FIGS. 1-4), the member 100 is mounted to the forward end of the utility rod 108, and so that one of the elongate pads 110, 112 engages the chest of the patient. When the patient is to undergo extension testing (FIG. 5), the member 100 is mounted to the rear end of the utility rod 108, and so that the other of the elongate pads 110, 112 engages the upper back of the patient.

Figures 12, 13, 14, 15, 16:
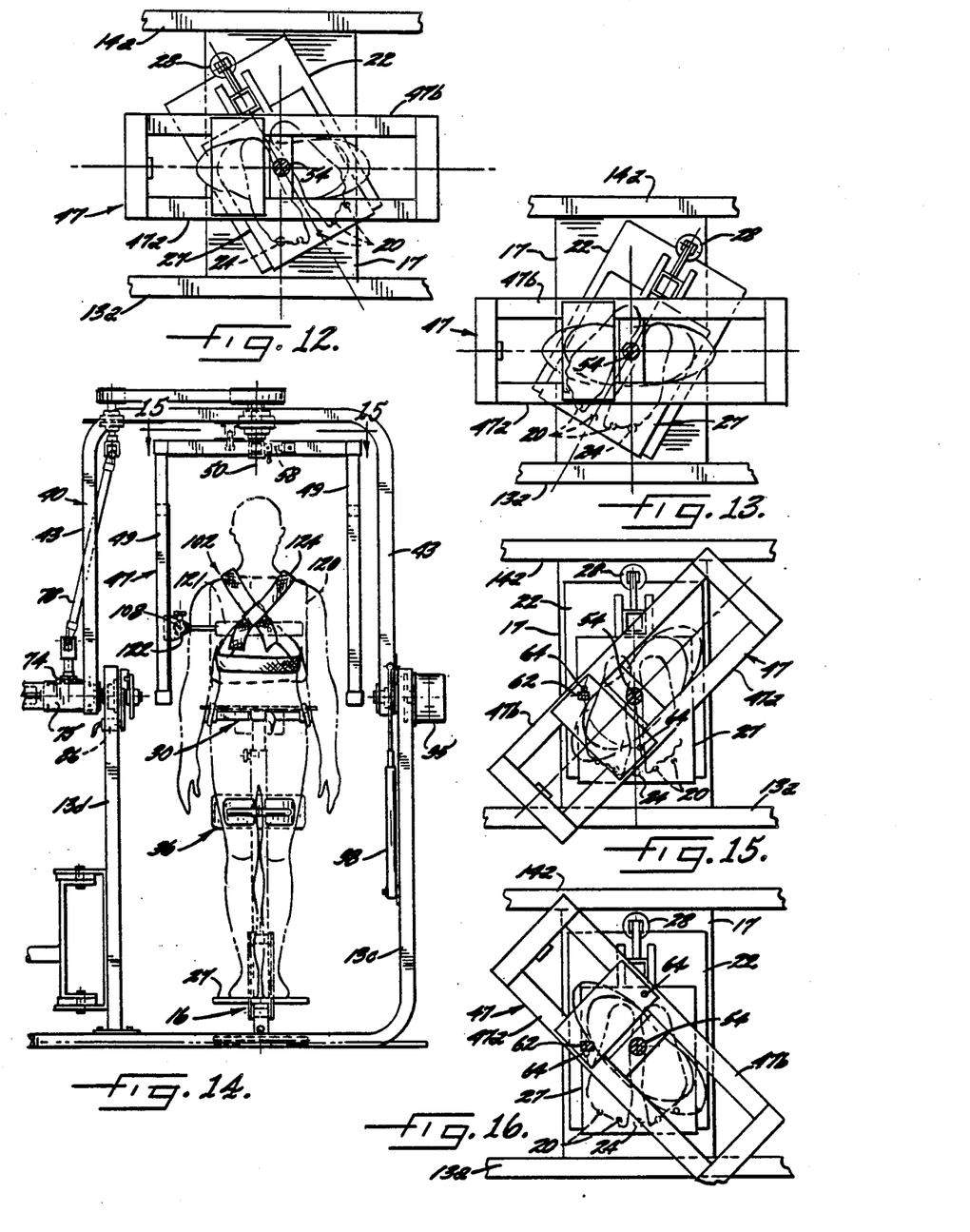
FIGS. 12-13 are views similar to FIG. 10, but illustrating the platform rotated and locked in the maximum left hand and right hand positions respectively.
FIG. 14 is a fragmentary view similar to FIG. 1, but illustrating the apparatus configured for the twisting mode.
FIGS. 15 and 16 are plan views of the upper body yoke taken substantially along the line 15—15 of FIG. 14, and illustrating the yoke rotated to the maximum left hand and right hand positions, respectively.

The second body engaging member 102 is used when the apparatus is configured for operation in the twisting mode (FIGS. 14-16). The second member 102 comprises a back pad 120 which is mounted to a support arm 121, and the free end of the arm 121 includes a mounting sleeve 122 and so that the member may be slidably mounted to the rear end of the utility rod. A chest harness 124 is fixed to the back pad 120, so that the upper body portion of the patient may be tightly held against the back pad 120 when the patient is standing upon the platform 27.

The dynamometer means of the present invention also includes a computer control system, which includes a predetermined program for monitoring the output signals from the operative load cells and potentiometers, and for controlling the operation of the drive motor 68 in accordance with the program. In this regard, the program may be designed for testing under isokinetic, isotonic, isometric conditions, or any other protocol. Also, in accordance with conventional technology, protocols may be employed which require the patient to perform an interactive task by monitoring the computer screen of the computer that controls and records the action of the drive motor. The computer terminal 125 may be conveniently positioned on a stand 127 which is pivotally mounted to the main frame of the apparatus as seen in FIG. 1, and so as to pivot about a vertical axis 128 and be movable to a position in front of the patient and thus readily visible.

FLEXION/EXTENSION OPERATION

When the apparatus 10 is to be operated in the flexion/extension mode as seen in FIGS. 1-9, the yoke 47 is rotated about the twisting axis 50 by the drive motor 68 so as to be positioned in the plane of the overhead frame member 40. In this regard, it will be understood that the yoke 47 is inherently locked against rotation about the twisting axis by pushing against the yoke, since the gear box 74 prevents backwards rotation therethrough. Also, the clutch 72 is engaged to lock the frame member 75 to the output shaft 69, and thus any rotation of the output shaft 69 of the drive motor will not be transmitted through the gear box since the gear box itself rotates.

The patient is then positioned to stand upon the platform 27, and the elevation thereof is adjusted by the operation of the linear actuator 28 until the juncture between the fixed vertebrae and moveable vertebrae of the spine (i.e. the lumbro-sacral junction at L5-S1) is approximately aligned with the horizontal axis 45. The pelvic stabilization assembly 30 is then adjusted in elevation and attached to the pelvic region of the patient, and the leg engaging assembly 36 is positioned to engage the legs. Next, the upper body engaging member 100 is mounted to either the front or rear end of the utility rod 108. More particularly, where flexion is to be monitored, the member 100 is mounted to the forward end of the rod and so that the pad 110 engages the chest of the patient. The elevation of the member 100 with respect to the chest may be adjusted by sliding the slide 105 along the plate 104. Where extension is to be monitored, the member 100 is mounted to the rear end of the rod 108, and so that the pad 112 engages the upper back of the patient at the selected elevation.

The apparatus 10 is then ready to be set into operation in accordance with the operating program provided by the computer control system. While in operation, the load cell 116 of the body engaging member 100 interfaces with the patient, and its output signal is fed to the computer control, along with a signal from the potentiometers 70, 86 which are indicative of the angular position of the drive motor 68 and the overhead frame member 40 respectively.

In order to operate in planes outside of the sagittal plane, the platform 27 is rotated and locked into one of the predetermined angular orientations as determined by the location of the openings 20 in the plate 17, and as illustrated in FIGS. 12 and 13.

TWISTING OPERATION

In the twisting mode (FIGS. 14-16), the patient is positioned to stand upon the platform 27, with the pelvic region and legs being stabilized by means of the pelvic stabilization assembly 30 and leg assembly 36 in the manner described above. In addition, the body engaging member 102 is mounted to the rear end of the utility rod 108, and the upper body of the patient is positioned so that the back of the patient is against the back pad 120 and the upper body is firmly pressed against the pad by the harness 124. Also, the patient is preferably positioned so that the twisting axis 50 is aligned along the lumbro-sacral axis of the patient.

The overhead frame member 40 is initially positioned in its fully upright position, although the frame member may be inclined from the fully upright position, if desired. The clutch 72 is disengaged, so that the output of the drive motor passes through the stationary gear box 74 to the drive shaft 78, the timing belt 83, the twist shaft 54, and thus to the yoke 47. The brake 95 is also operated, to firmly lock the overhead frame member in its fully upright, or other selected operating orientation.

Before initiating the operation, the start and stop twist angles are recorded by signals from the potentiometer 70, and during operation, the load cell 58 measures the torque the patient applies to the yoke 47, or the torque being applied to the patient, depending upon the programmed protocol. Also, the potentiometer 70 reads the angular position of the drive motor 68, as well as the twisting angle of the yoke 47 with respect to the overhead frame member, and the signals from the load cell and the potentiometer are fed to the computer control system.

In the drawings and specification, there has been set forth a preferred embodiment of the invention, and although specific terms are employed, they are used in a generic and descriptive sense only and not for purposes of limitation.

That which is claimed is:

1. An apparatus for monitoring the movement of the lumbar spine during flexion and extension of the trunk of a patient in each of several sagittal-frontal planes of the body, and comprising
   a main frame,
   a horizontal platform rotatably mounted to said main frame for rotation about a vertical axis and being adapted to support a patient in a standing position thereupon,
   means for locking said platform to said main frame in each of several predetermined rotational positions with respect to said main frame,
   pelvic stabilization means mounted to said platform for releasable connection to the pelvic region of the trunk of a patient standing upon said platform so as to support the pelvic region of the trunk in a fixed position with respect to said platform,
   a frame member mounted to said main frame for rotation about a horizontal axis which is positioned to pass approximately through the lumbro-sacral junction of a patient while the patient is standing upon said platform and supported by said pelvic stabilization means,
   upper body engaging means mounted to said frame member for engaging the upper body portion of a patient standing upon said platform and so that flexion and extension of the trunk of the patient causes said frame member to pivot about said horizontal axis in at least one direction, and
   dynamometer means operatively connected to said frame member for controlling the pivotal movement thereof in each pivotal direction,
   whereby the platform may be selectively moved to each of said predetermined rotational positions and the patient permitted to perform flexion and extension of the trunk about said horizontal axis while the platform is in each of said positions, and while said dynamometer means controls the pivotal movement of said frame member.

2. The apparatus as defined in claim 1 further comprising means mounting said platform to said main frame so as to permit vertical adjustment of the height thereof, and means mounting said pelvic stabilization means to said platform so as to permit vertical adjustment of said pelvic stabilization means with respect to said platform, whereby the apparatus may be configured to accommodate patients of varying height.

3. The apparatus as defined in claim 2 wherein said pelvic stabilizing means further comprises means for engaging and supporting the legs of the patient at a location immediately above the knees, and so as to maintain the legs in a locked fully extended position.

4. The apparatus as defined in claim 1 wherein said upper body engaging means comprises an elongate pad assembly, and means mounting said pad assembly to said frame member at an adjustable location along a line extending perpendicularly to said horizontal axis and generally between the back and front of the patient standing upon said platform, and whereby said elongate pad assembly may be positioned to engage either the chest or the upper back of the patient.

5. The apparatus as defined in claim 1 further comprising means to physically limit the rotation of said frame member about said horizontal axis to a selected angular rotation in each direction from a fully upright position.

6. The apparatus as defined in claim 1 wherein said dynamometer means comprises
   force transducer means for measuring the force applied between said frame member and the patient during flexion and extension of the trunk,
   potentiometer means for monitoring the angular position of said frame member,
   a reversible drive motor operatively connected to pivot said frame member about said horizontal axis, and
   computer control means including a predetermined program for monitoring the output signals from said force transducer means and said potentiometer means, and for controlling the operation of said drive motor in accordance with said program.

7. The apparatus as defined in claim 6 wherein said force transducer means comprises a load cell mounted to said elongate pad assembly.

8. An apparatus for monitoring the movement of the lumbar spine during flexion and extension of the trunk of a patient, and during trunk twisting, and comprising
   a main frame,
   a horizontal platform mounted to said main frame and being adapted to support a patient in a standing position thereupon,
   pelvic stabilization means for releasable connection to the pelvic region of the trunk of a patient standing upon said platform so as to support the pelvic region of the trunk in a fixed position with respect to said main frame,
   an overhead frame member having a generally inverted U-shaped outline and comprising a horizontal beam and two depending legs,
   means mounting said overhead frame member to said main frame for movement about a horizontal axis which is positioned to pass approximately through the lumbro-sacral junction of a patient while the patient is standing upon said platform and supported by said pelvic stabilization means, and with said horizontal axis extending through both of said depending legs and with said horizontal beam being parallel to and above said horizontal axis, an upper body yoke mounted to said horizontal beam of said overhead frame member for rotation about a twisting axis which is generally vertical and perpendicular to said horizontal axis, means for selectively converting said apparatus to a first configuration wherein said upper body yoke is locked against rotation about said twisting axis while said overhead frame member is free to rotate about said horizontal axis, or to a second configuration wherein said overhead frame member is locked against rotation about said horizontal axis while said yoke is free to rotate about said twisting axis, upper body engaging means mounted to said upper body yoke for engaging the upper body portion of a patient standing upon said platform and so that in said first configuration flexion and extension of the trunk of the patient causes said overhead frame member to pivot about said horizontal axis in at least one direction, and in said second configuration twisting of the trunk of the patient causes said upper body yoke to twist about said twisting axis, dynamometer means for controlling pivotal movement of said overhead frame member when in said first configuration, and for controlling twisting movement of said upper body yoke in said second configuration, whereby in the first configuration the patient is permitted to perform flexion and extension of the trunk about said horizontal axis while said dynamometer means controls the pivotal movement of said overhead frame member, and in said second configuration the patient is permitted to perform twisting of the trunk and while said dynamometer means controls the twisting movement of said upper body yoke.

9. The apparatus as defined in claim 8 further comprising means mounting said platform to said main frame so as to permit vertical adjustment of the height thereof, and means mounting said pelvic stabilization means to said platform so as to permit vertical adjustment of said pelvic stabilization means with respect to said platform, whereby the apparatus may be configured to accommodate patients of varying height.

10. The apparatus as defined in claim 9 wherein said pelvic stabilizing means further comprises means for engaging and supporting the legs of the patient at a location immediately above the knees, and so as to maintain the legs in a fully extended position.

11. The apparatus as defined in claim 8 wherein said upper body engaging means comprises a first member composed of an elongate pad assembly, and means for releasably mounting said first member to said upper body yoke at an adjustable location along a line extending perpendicular to said horizontal axis and generally between the back and front of the patient standing upon said platform, and whereby said elongate pad assembly may be positioned to engage either the chest or the upper back of the patient when said apparatus is in said first configuration, and a second member composed of a back pad and a chest harness mounted to said back pad, and means for releasably mounting said second member to said upper body yoke, and whereby said second member is useable when said apparatus is in said second configuration so that the patient may impart twist to said upper body yoke.

12. The apparatus as defined in claim 8 further comprising means to physically limit the rotation of said overhead frame member about said horizontal axis to a selected angular rotation in each direction from a fully upright position, and means to physically limit the rotation of said yoke in each direction about said twisting axis.

13. The apparatus as defined in claim 8 wherein said dynamometer means comprises first force transducer means for measuring the force applied between said overhead frame member and the patient when said apparatus is in said first configuration, second force transducer means for measuring the twisting force applied between said upper body yoke and the patient when said apparatus is in said second configuration, first potentiometer means for monitoring the angular position of said overhead frame member when said apparatus is in said first configuration, second potentiometer means for monitoring the angular position of said yoke when said apparatus is in said second configuration, a reversible drive motor, clutch means for operatively connecting said drive motor to pivot said overhead frame member about said horizontal axis in said first configuration, and for operatively connecting said drive motor to said yoke in said second configuration, and computer control means including a predetermined program for monitoring the output signals from said first and second force transducer means and said first and second potentiometer means, and for controlling the operation of said drive motor in accordance with said program when said apparatus is in each of said first and second configurations.

14. An apparatus for monitoring the movement of the lumbar spine during flexion and extension of the trunk of a patient in each of several sagittal-frontal planes of the body, and during trunk twisting, and comprising a main frame, a horizontal platform rotatably mounted to said main frame for rotation about a vertical axis and being adapted to support a patient in a standing position thereupon, means for locking said platform to said main frame in each of several predetermined rotational positions with respect to said main frame, pelvic stabilization means mounted to said platform for releasable connection to the pelvic region of the trunk of a patient standing upon said platform so as to support the pelvic region of the trunk in a fixed position with respect to said platform, an overhead frame member having a generally inverted U-shaped outline and comprising a horizontal beam and two depending legs, means mounting said overhead frame member to said main frame for movement about a horizontal axis which is positioned to pass approximately through the lumbro-sacral junction of a patient while the patient is standing upon said platform and supported by said pelvic stabilization means, and with said horizontal axis extending through both of said depending legs and with said horizontal beam being parallel to and above said horizontal axis, an upper body yoke mounted to said horizontal beam of said overhead frame member for rotation about a twisting axis which is adapted to be aligned along the lumbro-sacral axis of the patient, and which is generally vertical and perpendicular to said horizontal axis, means for selectively converting said apparatus to a first configuration wherein said upper body yoke is locked against rotation about said twisting axis while said overhead frame member is free to rotate about said horizontal axis, or to a second configuration wherein said overhead frame member is locked against rotation about said horizontal axis while said yoke is free to rotate about said twisting axis, upper body engaging means mounted to said upper body yoke for engaging the upper body portion of a patient standing upon said platform and so that in said first configuration flexion and extension of the trunk of the patient causes said overhead frame member to pivot about said horizontal axis in at least one direction, and in said second configuration twisting of the trunk of the patient causes said upper body yoke to twist about said twisting axis, dynamometer means for controlling pivotal movement of said overhead frame member when in said first configuration, and for controlling twisting movement of said upper body yoke in said second configuration, whereby in the first configuration the platform may be selectively moved to each of said predetermined rotational positions and the patient permitted to perform flexion and extension of the trunk about said horizontal axis while the platform is in each of said positions, and while said dynamometer means controls the pivotal movement of said overhead frame member, and in said second configuration the patient is permitted to perform twisting of the trunk and while said dynamometer means controls the twisting movement of said upper body yoke.

15. An apparatus for monitoring the movement of a patient during trunk twisting, and comprising a main frame, a horizontal platform mounted to said main frame and being adapted to support a patient in a standing position thereupon, an overhead frame member, means mounting said overhead frame member to said main frame for movement about a horizontal axis which is positioned to pass approximately through the lumbro-sacral junction of a patient while the patient is standing upon said platform, an upper body engaging member, means mounting said upper body engaging member to said overhead frame member for rotation about a twisting axis which is generally perpendicular to said horizontal axis, means for selectively pivoting said overhead frame member about said horizontal axis and retaining the same in a selected angular orientation, while said upper body engaging member remains free to rotate about said twisting axis, and dynamometer means for controlling twisting movement of said upper body engaging member about said twisting axis, whereby the patient is permitted to perform twisting of the trunk while the body is retained in the selected angular orientation about said horizontal axis and while said dynamometer means controls the twisting movement of said upper body engaging member.

16. The apparatus as defined in claim 15 further comprising means to physically limit the rotation of said overhead frame member to a selected angular rotation in each direction about said horizontal axis, and means to physically limit the rotation of said upper body engaging member in each direction about said twisting axis.

17. The apparatus as defined in claim 16 further comprising pelvic stabilization means for releasable connection to the pelvic region of the trunk of a patient standing upon said platform so as to support the pelvic region of the trunk in a fixed position with respect to said main frame.

18. The apparatus as defined in claim 17 further comprising means mounting said platform to said main frame so as to permit vertical adjustment of the height thereof, whereby the apparatus may be configured to accommodate patients of varying height.

19. The apparatus as defined in claim 15 wherein said means mounting said upper body engaging member comprises a yoke which includes an overhead arm and a depending arm, with said overhead arm being pivotally mounted to said overhead frame member for rotation about said twisting axis, and with said upper body engaging member being mounted to said depending arm.

20. The apparatus ad defined in claim 19 wherein said upper body engaging member comprises a back pad and a chest harness mounted to said back pad, and means mounting said back pad to said depending arm of said yoke.

21. The apparatus as defined in claim 15 wherein said dynamometer means comprises force transducer means for measuring the twisting force applied between said upper body engaging member and the patient, potentiometer means for monitoring the angular position of said upper body engaging member about said twisting axis, reversible drive motor means operatively connected to said upper body engaging member for rotating the same about said twisting axis, and computer control means including a predetermined program for monitoring the output signals from said force transducer means and said potentiometer means, and for controlling the operation of said drive motor in accordance with said program.

22. The apparatus as defined in claim 15 wherein said horizontal platform is mounted to said main frame for rotation about a vertical axis, and said apparatus further comprises means for locking said platform to said main frame in a selected rotational position with respect to said main frame.

* * * * *